(12) United States Patent
Van Landuyt

(10) Patent No.: US 6,761,170 B2
(45) Date of Patent: Jul. 13, 2004

(54) LARYNGEAL MASK ASSEMBLIES

(75) Inventor: Christophe Van Landuyt, London (GB)

(73) Assignee: Smiths Group PLC, London (GB)

( * ) Notice: Subject to any disclaimer, the term of this patent is extended or adjusted under 35 U.S.C. 154(b) by 182 days.

(21) Appl. No.: 10/060,364

(22) Filed: Feb. 1, 2002

(65) Prior Publication Data

US 2002/0112728 A1 Aug. 22, 2002

(30) Foreign Application Priority Data

Feb. 16, 2001 (GB) .............................................. 0103815

(51) Int. Cl.⁷ .......................... A61M 16/00; A62B 9/06
(52) U.S. Cl. .............................. 128/207.14; 128/207.15
(58) Field of Search ......................... 128/207.14, 207.15

(56) References Cited

U.S. PATENT DOCUMENTS

| 5,771,889 A | * | 6/1998 | Pagan | .................... | 128/207.15 |
| 5,878,745 A | * | 3/1999 | Brain | .................... | 128/207.15 |
| 5,896,858 A | * | 4/1999 | Brain | .................... | 128/207.15 |
| 6,050,264 A | * | 4/2000 | Greenfield | ............. | 128/207.15 |
| 6,095,144 A | * | 8/2000 | Pagan | .................... | 128/207.15 |

FOREIGN PATENT DOCUMENTS

| GB | 2317342 | 3/1998 |
| GB | 2323289 | 9/1998 |
| GB | 2324737 | 11/1998 |
| GB | 2331932 | 6/1999 |
| WO | WO 97/12641 | 4/1997 |

\* cited by examiner

Primary Examiner—Glenn K. Dawson
Assistant Examiner—Darwin P Erezo
(74) Attorney, Agent, or Firm—Louis Woo

(57) ABSTRACT

A laryngeal mask assembly has a tube with a mask at one end defining a cavity surrounded by a sealing cuff. A blocker is operable to prevent entry of the epiglottis into the cavity during insertion of the assembly but does not hinder gas passage along the assembly after insertion. The blocker may be a ballon that is inflated during insertion and is then deflated. Alternatively, the blocker may be a web attached to the patient end of the assembly by a rupturable joint. In another arrangement the blocker is an insert with an end that expands to fill the cavity but that is compressible to allow the insert to be pulled out from the machine end of the assembly.

4 Claims, 2 Drawing Sheets

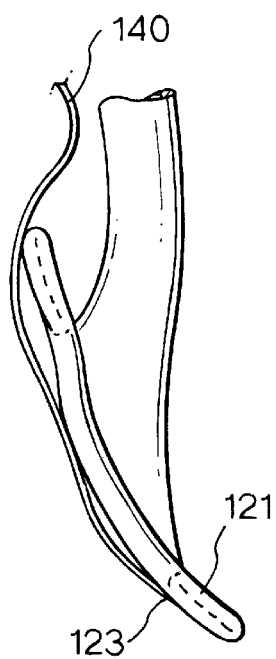
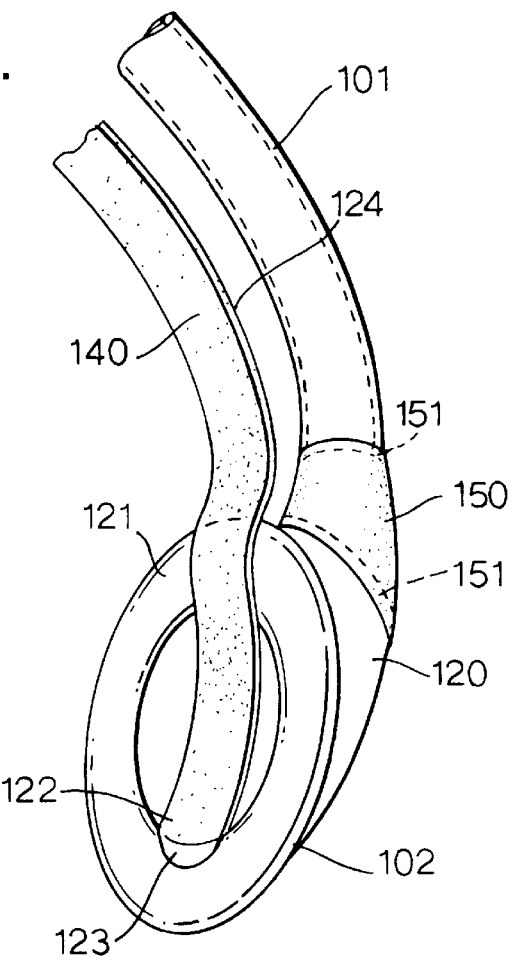
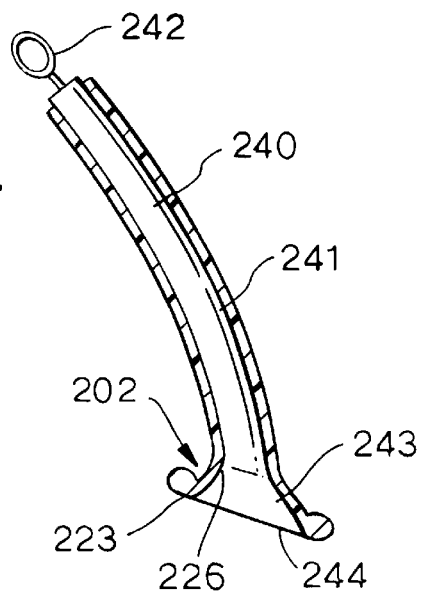

LARYNGEAL MASK ASSEMBLIES

BACKGROUND OF THE INVENTION

This invention relates to laryngeal mask assemblies and their manufacture

It is common practice to use an airway known as a laryngeal mask for administering anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2249959, GB 2111394, EP 448878, U.S. Pat. No. 4,995,388, GB 2205499, GB 2128561, GB 2298797, GB 2334215, GB 0020274 and GB 0002805.

Laryngeal masks have several advantages over endotracheal tubes, which are longer and seal with the trachea below the vocal folds. One potential problem with laryngeal masks is that there is a risk that they may be blocked by the epiglottis during insertion.

BRIEF SUMMARY OF THE INVENTION

It is an object of the present invention to provide an alternative laryngeal mask assembly.

According to the present invention there is provided a laryngeal mask assembly comprising a tube, a mask at the patient end of the tube, an annular cuff extending around the patient end of the mask, and an internal cavity within the mask communicating with the tube at one end and opening from the assembly at its other end within a central region of the cuff, the assembly including blocking means that can be put in a first state where it prevents entry of the epiglottis into the cavity or a second state where the cavity is substantially open.

The blocking means may be an expansible member that is expanded in the first state and is retracted in the second state. The expansible member may be a balloon of an elastic material. The expansible member may be attached with the mask and communicate with an inflation lumen extending along the mask and tube. Alternatively, the blocking means could include a removable member such as a web extending across the patient end of the assembly. The removable member may be retained at its patient end with the mask by a rupturable joint and the assembly may include a non-elastic cord by which the rupturable joint can be torn from the machine end of the assembly. Alternatively, the removable member may be an insert extending along the tube, the insert having a portion expanded within the cavity, which portion provides an end surface substantially level with the patient end of the mask. The insert preferably includes a foam or gel. The mask preferably includes a mount on which the cuff is supported, and the assembly preferably has a region towards the mount that is resiliently flexible.

A laryngeal mask assembly according to the present invention will now be described, by way of example, with reference to the accompanying drawings.

BRIEF DESCRIPTION OF THE DRAWINGS

FIG. 3 is a perspective view of an alternative assembly;

FIG. 4 is a side elevation view of the assembly of FIG. 3; and

FIG. 5 is a sectional side elevation view of a second alternative assembly.

DETAILED DESCRIPTION OF PREFERRED EMBODIMENTS

Figure 1:
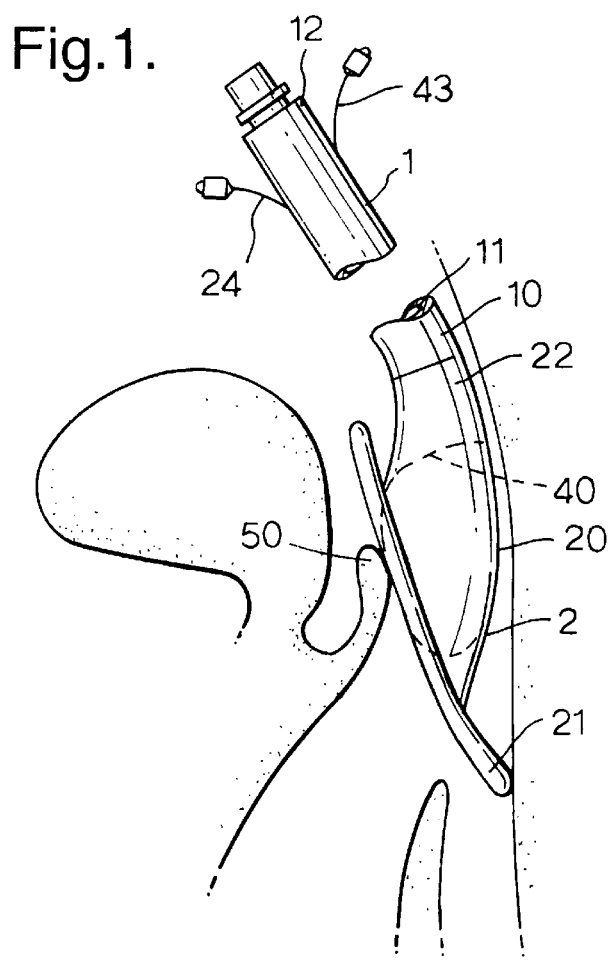
FIG. 1 is a side elevation view of the assembly.
Figure 2:
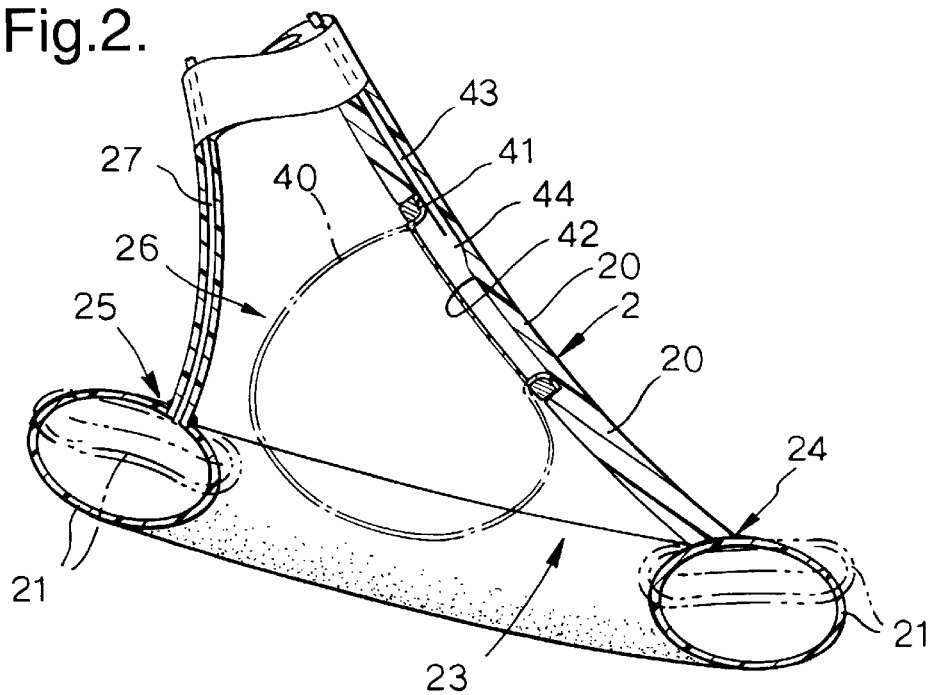
FIG. 2 is an enlarged cross-sectional, side elevation view of the patient end of the assembly.

With reference first to FIGS. 1 and 2, the laryngeal mask assembly comprises a tube 1 and a mask 2 mounted at the patient end 10 of the tube.

The tube 1 is of a bendable plastics material, such as PVC and is curved along its length. A bore 11 extends along the tube from its patient end 10 to its rear, machine end 12.

The mask 2 includes a mount 20 and an inflatable sealing cuff 21. The mount 20 is of a relatively stiff plastics material and is of generally shoe shape. The rear, machine end of the mount has a neck 22 of circular section embracing and bonded to the patient end 10 of the tube 1. The mount 20 tapers outwardly from the machine end 22 to its patient end opening 23, which is inclined to the axis of the machine end at an angle of about 25° so that the patient end of the mount has an oval shape with its forward end 24 being more pointed than its rear end 25. The patient end 23 of the mount 20 is inclined to face towards the inner side of the curve of the tube 1. Internally, the machine end 22 of the mount 20 communicates with a cavity 26 in the mount that increases in cross-sectional area along its length, from the machine end.

The cuff 21 is tubular and of a thin flexible plastics material formed into an annulus of the same shape as the patient end 23 of the mount 20. The cuff 21 is attached around the patient end 23 of the mount 20 such as by means of an adhesive. The cuff 21 is inflated and deflated by means of an inflation lumen 24 extending within the wall of the main tube and through a small bore inflation tube. When inflated in position in a patient, the cuff 21 expands to contact patient tissue in the region of the hypopharnyx.

The assembly additionally includes blocking means in the form of an inflatable balloon 40 within the mount 20. The balloon 40 is in the form of a membrane of elastic material of generally circular shape and attached around its edge 41 in a shallow recess 42 on the inside surface of the mount 20 facing generally towards the opening 23. A second inflation lumen 43 extends along the tube 1 and mount 20, opening through an aperture 44 within the recess 42. The balloon 40 is inflated by supplying air or other fluid along the inflation lumen 43 in the usual way, so that the balloon expands to a first state (as indicated by the broken line in FIG. 2) where it substantially fills the cavity 26 and comes substantially level with the patient end 23 of the mask 2. When air is released from the inflation lumen 43, the resilience of the balloon 40 causes it to retract to a second state where it lies flat against the internal surface of the mount 20. When the laryngeal mask is inserted, the balloon 40 is inflate to its first state so that it blocks entry of the epiglottis 50. Once inserted to the correct position, the balloon 40 is deflated to its second state so that it provides no substantial obstruction within the mask 2.

This arrangement reduces the risk of the epiglottis being caught by the laryngeal mask and folded down during insertion where it would potentially block passage through the assembly. Because the blocking means is retracted after insertion, it does not provide any obstruction to gas flow, visualisation or the insertion of devices along the laryngeal mask during use.

There are various other ways in which blocking means could be provided in a laryngeal mask. For example, as shown in FIGS. 3 and 4, the blocking means could be provided by a removable member such as in the form of a web or strip 140 extending loosely along the outside of the assembly, over the rear end of the cuff 121 and attached at its patient end 122 to the inside surface of the mount 120, by a rupturable joint 123 close to the cuff. A non-elastic string 124 extends loosely along the web 140 and is attached at its patient end to the rupturable joint 123 so that the joint can be torn readily by pulling the rear, machine end of the string. The web 140 acts to block entrance of the epiglottis during insertion of the assembly.

The assembly also has a resilient portion or hinge 150 formed by a region towards the mask 102 of an elastomeric material substantially more flexible and resilient than the remainder of the assembly. The hinge 150 takes the form of a short tubular portion between the patient end of the tube 101 and the machine end of the mount 120. Each end of the hinge portion 150 has a key formation 151, which securely attaches it to the tube 101 and mount 120. Preferably, the elastic material of the hinge 150 is formed during a two-stage moulding operation with the tube 101 and or alternatively the mount 120, or both. The web 140 may be pulled to displace the patient end of the mask 102 anteriorly in order to facilitate insertion. The flexible hinge 150 enables the mask 102 more readily to follow the pharyngeal anatomy of the patient during insertion. Once inserted, the clinician pulls the string 124 to release the joint 123 so that the web 140 can be pulled out. Even without the web, the hinge 150 can reduce the risk of the epiglottis projecting into the patient end of the mask 102 because, during insertion, the mask can follow a path further to the posterior of the epiglottis.

In a further embodiment, shown in FIG. 5, the blocking means is an insert member 240 insertable within the assembly. The insert 240 has a main, flexible tubular portion 241, a handle 242 at its rear or machine end and a blocking portion 243 at its forward or patient end. The blocking portion 243 is compressible, such as by being of a foam or having a gel sack, and has a natural, generally conical shape so that it substantially fills the cavity 226 of the mask 202 and has a patient end surface 244 substantially level with the end 223 of the mask. This end surface 244 provides a soft, atraumatic surface that effectively prevents entry of the epiglottis into the cavity 226 of the mask 202 during insertion of the assembly. Once inserted, the insert 240 is readily removed simply by pulling the handle 242. As it is pulled out, the blocking portion 243 compresses to a smaller size during passage along the tube 201. The insert could have an airway passage extending along it to permit breathing by the patient before removal of the insert.

What I claim is:

1. A laryngeal mask assembly comprising: a tube; a mask at a patient end of said tube; a sealing cuff extending around a patient end of said mask; and an internal cavity within said mask, said cavity having a first end and a second end opposite said first end, said first end communicating with said tube and said second end opening from said assembly within a central region of said cuff, wherein said assembly includes an insert extending along the tube and having a patient end expanded substantially to fill the cavity so as to prevent entry of the epiglottis into said cavity during insertion of said assembly, said patient end of said insert being compressible to allow the insert to be pulled out of the assembly from the machine end of the assembly.

2. An assembly according to claim 1, wherein said mask includes a mount on which said cuff is supported, and wherein said assembly has a region towards said mount that is resiliently flexible.

3. A laryngeal mask assembly according to claim 1, wherein said patient end of said insert is arranged to provide an end surface substantially level with the patient end of said mask.

4. A laryngeal mask assembly according to claim 1, wherein said patient end of said insert includes a foam or a gel.

\* \* \* \* \*